(12) United States Patent
Xu

(10) Patent No.: US 11,736,855 B1
(45) Date of Patent: Aug. 22, 2023

(54) COMMUNICATION DEVICE AND SYSTEM FOR CONNECTING COMMUNICATION DEVICE TO HEARING PROTECTION EQUIPMENT

(71) Applicant: Hangzhou ZH Tech Co., Ltd., Zhejiang (CN)

(72) Inventor: Hanwen Xu, Zhejiang (CN)

(73) Assignee: Hangzhou ZH Tech Co., Ltd., Hangzhou (CN)

( * ) Notice: Subject to any disclaimer, the term of this patent is extended or adjusted under 35 U.S.C. 154(b) by 0 days.

(21) Appl. No.: 18/109,259

(22) Filed: Feb. 13, 2023

(30) Foreign Application Priority Data

Jan. 10, 2023 (CN) .......................... 202320075791.9

(51) Int. Cl.
| | |
|---|---|
| H04R 1/10 | (2006.01) |
| H04R 1/02 | (2006.01) |
| H04R 1/04 | (2006.01) |
| A61F 11/14 | (2006.01) |

(52) U.S. Cl.
CPC .......... *H04R 1/1058* (2013.01); *A61F 11/145* (2022.01); *H04R 1/021* (2013.01); *H04R 1/028* (2013.01); *H04R 1/04* (2013.01); *H04R 2201/02* (2013.01); *H04R 2499/11* (2013.01)

(58) Field of Classification Search
CPC ...... H04R 1/1058; H04R 1/021; H04R 1/028; H04R 1/04; H04R 2201/02; H04R 2499/11; A61F 11/145
See application file for complete search history.

(56) References Cited

U.S. PATENT DOCUMENTS

| | | | | |
|---|---|---|---|---|
| 5,469,505 A * | 11/1995 | Gattey | ..................... | H04M 1/05 D14/206 |
| 5,835,609 A * | 11/1998 | LeGette | ................... | A61F 11/14 2/209 |
| 5,862,241 A * | 1/1999 | Nelson | ................. | H04R 1/1066 381/374 |
| 7,171,698 B2 * | 2/2007 | Saffran | .................... | A61F 11/14 2/209 |
| 8,213,667 B2 * | 7/2012 | Nelson | .................... | F16C 11/06 381/370 |
| 9,445,182 B2 * | 9/2016 | Pizzaro | ................ | H04R 1/1008 |
| 10,779,071 B2 * | 9/2020 | Wu | ........................ | H04R 1/105 |
| 11,477,575 B2 * | 10/2022 | Degner | ................ | H04R 5/0335 |

(Continued)

Primary Examiner — Oyesola C Ojo

(57) ABSTRACT

The present disclosure provides a communication device for a hearing protection equipment which includes at least one earmuff, at least one loudspeaker and an audio input member, the device includes: a housing; a first mounting assembly rotatably arranged on the housing; a second mounting assembly arranged on the housing, the first mounting assembly and the second mounting assembly are releasably connected to two ends of the earmuff respectively; a microphone configured for capturing an audio; a radio transceiver configured for wirelessly transmitting the audio captured by the microphone to user and wirelessly receiving a wireless signal containing an audio from the user; and an audio output member communicated with the audio input member and configured for transmitting the wireless signal containing the audio to the at least one loudspeaker. The present disclosure further provides a system for connecting the communication device to the hearing protection equipment.

19 Claims, 11 Drawing Sheets

(56) References Cited

U.S. PATENT DOCUMENTS

| | | | |
|---|---|---|---|
| 2011/0026726 A1* | 2/2011 | Kuo | H04R 1/1041 |
| | | | 381/375 |
| 2011/0051976 A1* | 3/2011 | Tsai | H04R 1/1066 |
| | | | 381/378 |
| 2018/0176673 A1* | 6/2018 | Madsen | H04R 1/1008 |
| 2021/0260414 A1* | 8/2021 | Mundy | A62B 18/003 |
| 2022/0353596 A1* | 11/2022 | Kuraoka | H04R 1/105 |

\* cited by examiner

COMMUNICATION DEVICE AND SYSTEM FOR CONNECTING COMMUNICATION DEVICE TO HEARING PROTECTION EQUIPMENT

CROSS REFERENCE TO RELATED APPLICATIONS

The present application claims the benefit of Chinese Utility Model Application No. 202320075791.9 filed on Jan. 10, 2023, the contents of which are incorporated herein by reference in their entirety.

FIELD

The present disclosure relates to communication transceivers and in particular to a communication device for hearing protection equipment, and a system for connecting a communication device to a hearing protection equipment.

BACKGROUND

Personal protective equipment, such as earmuffs or earplugs, are recommended for use in environments where people are exposed to harmful or potentially harmful decibel levels. In general, this equipment protects users by providing a barrier which reduces the level of noise or other sounds that is able to reach the users' ears. Users often equip the equipment with a communication device, so they can use their mobile phones normally when wearing the equipment. However, the existing communication device has a low adaptability and can only be installed on the equipment of a specific size, and the installation process is also inconvenient.

SUMMARY

The present disclosure provides a communication device for a hearing protection equipment which includes at least one earmuff, at least one loudspeaker and an audio input member, the device includes: a housing; a first mounting assembly rotatably arranged on the housing; a second mounting assembly arranged on the housing, the first mounting assembly and the second mounting assembly are releasably connected to two ends of the earmuff respectively; a microphone configured for capturing an audio; a radio transceiver configured for wirelessly transmitting the audio captured by the microphone to user and wirelessly receiving a wireless signal containing an audio from the user; and an audio output member communicated with the audio input member and configured for transmitting the wireless signal containing the audio to the at least one loudspeaker. The present disclosure further provides a system connecting the communication device to the hearing protection equipment.

The present disclosure further provides a system for connecting a communication device to a hearing protection equipment, the system includes a communication device and a hearing protection equipment. The communication device includes a housing, a first mounting assembly rotatably arranged on a first end of the housing, and a second mounting assembly arranged on a second end of the housing. The hearing protection equipment includes at least one earmuff having two fixing parts, the first mounting assembly and the second mounting assembly are installed on the two fixing parts respectively, to connect the communication device to the hearing protection equipment.

BRIEF DESCRIPTION OF THE DRAWINGS

Implementations of the present disclosure will now be described, by way of embodiment, with reference to the attached FIGS. It should be understood, the drawings are shown for illustrative purpose only, for ordinary person skilled in the art, other drawings obtained from these drawings without paying creative labor by an ordinary person skilled in the art should be within scope of the present disclosure.

Figure 1:
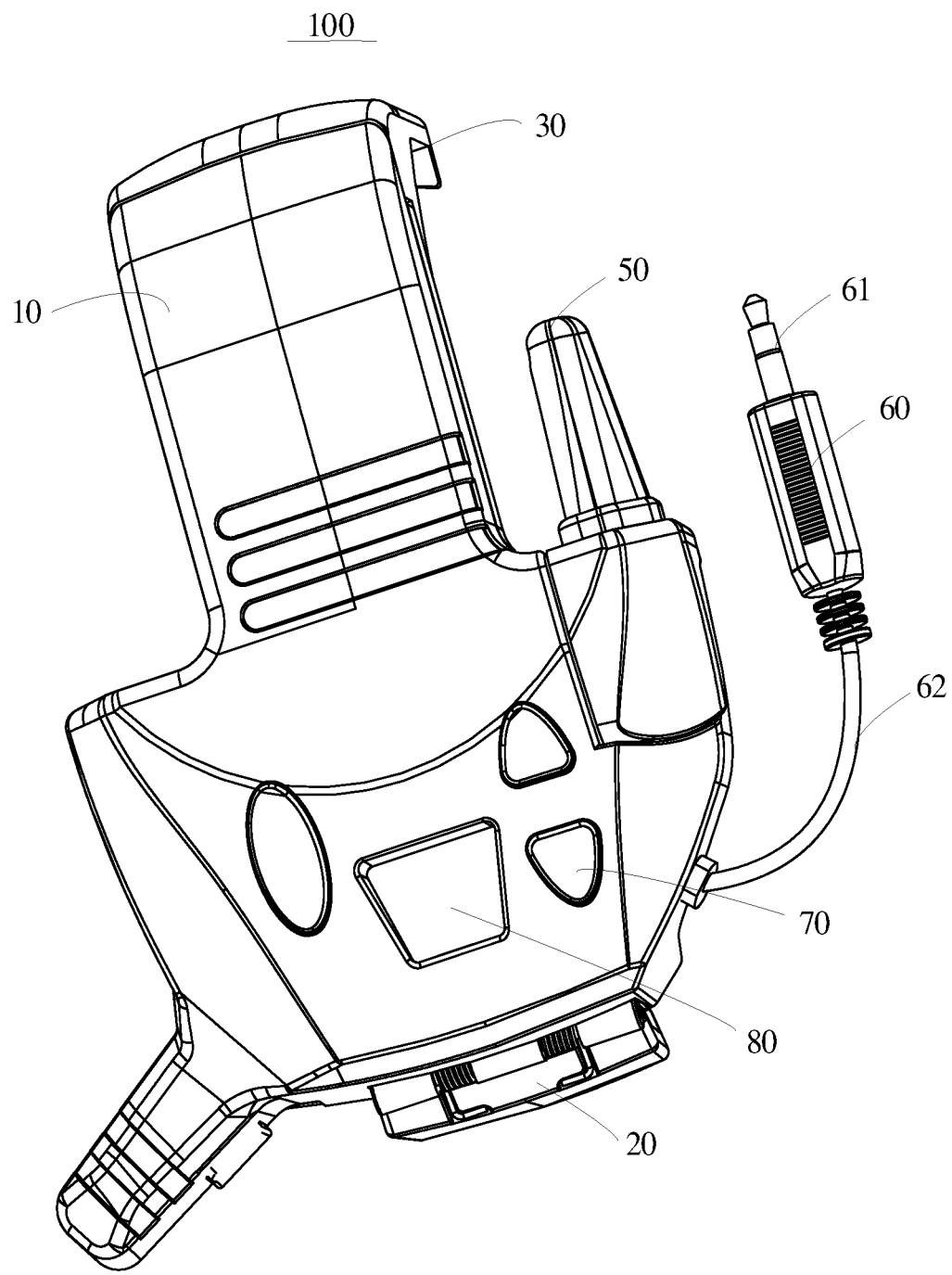
FIG. 1 is a structure diagram of a communication device according to an embodiment of the present disclosure.
Figure 2:
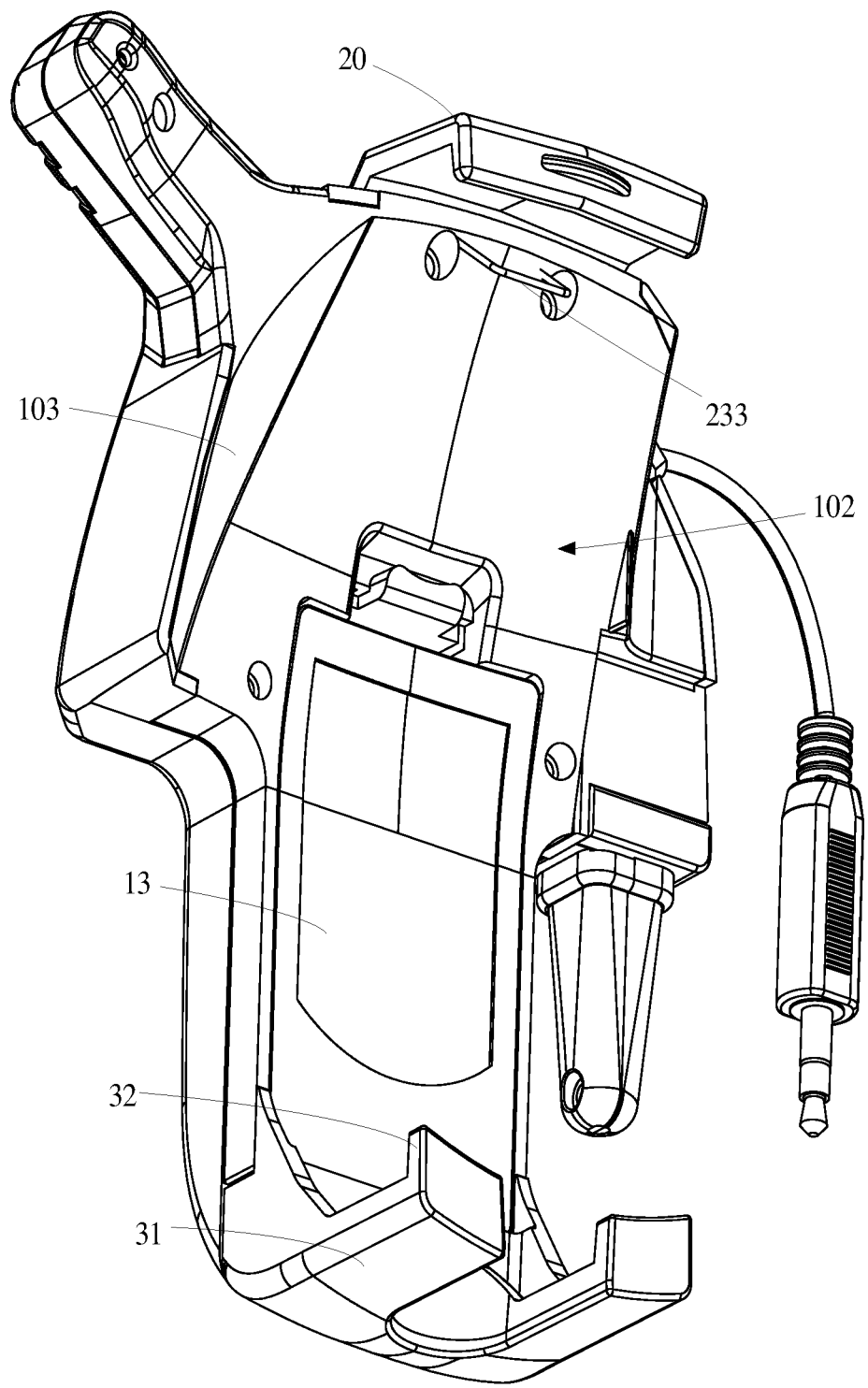
FIG. 2 is another structure diagram of the communication device of FIG. 1.
Figure 3:
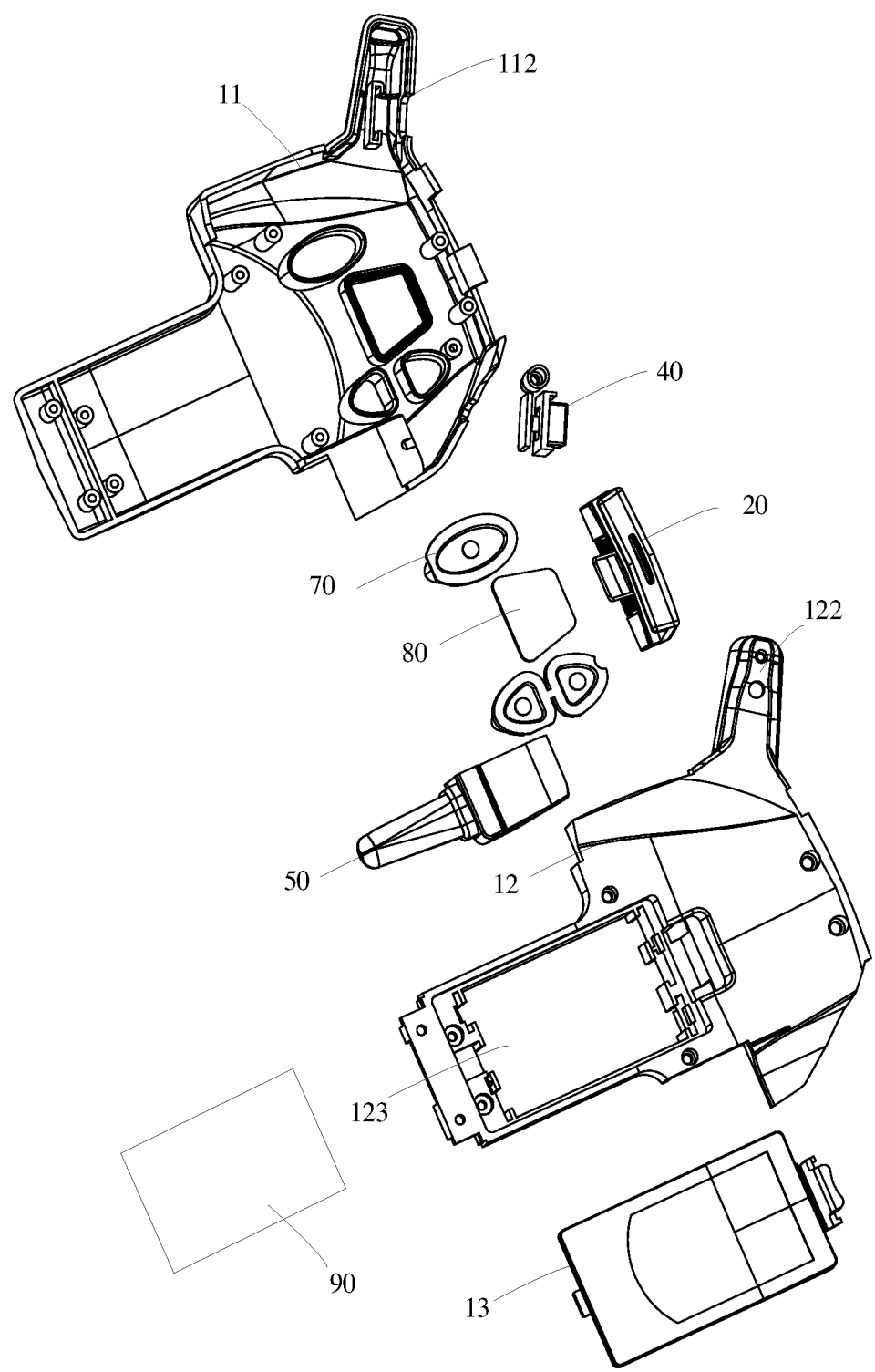
FIG. 3 is an exploded diagram of a part of the communication device in FIG. 1.
Figure 4:
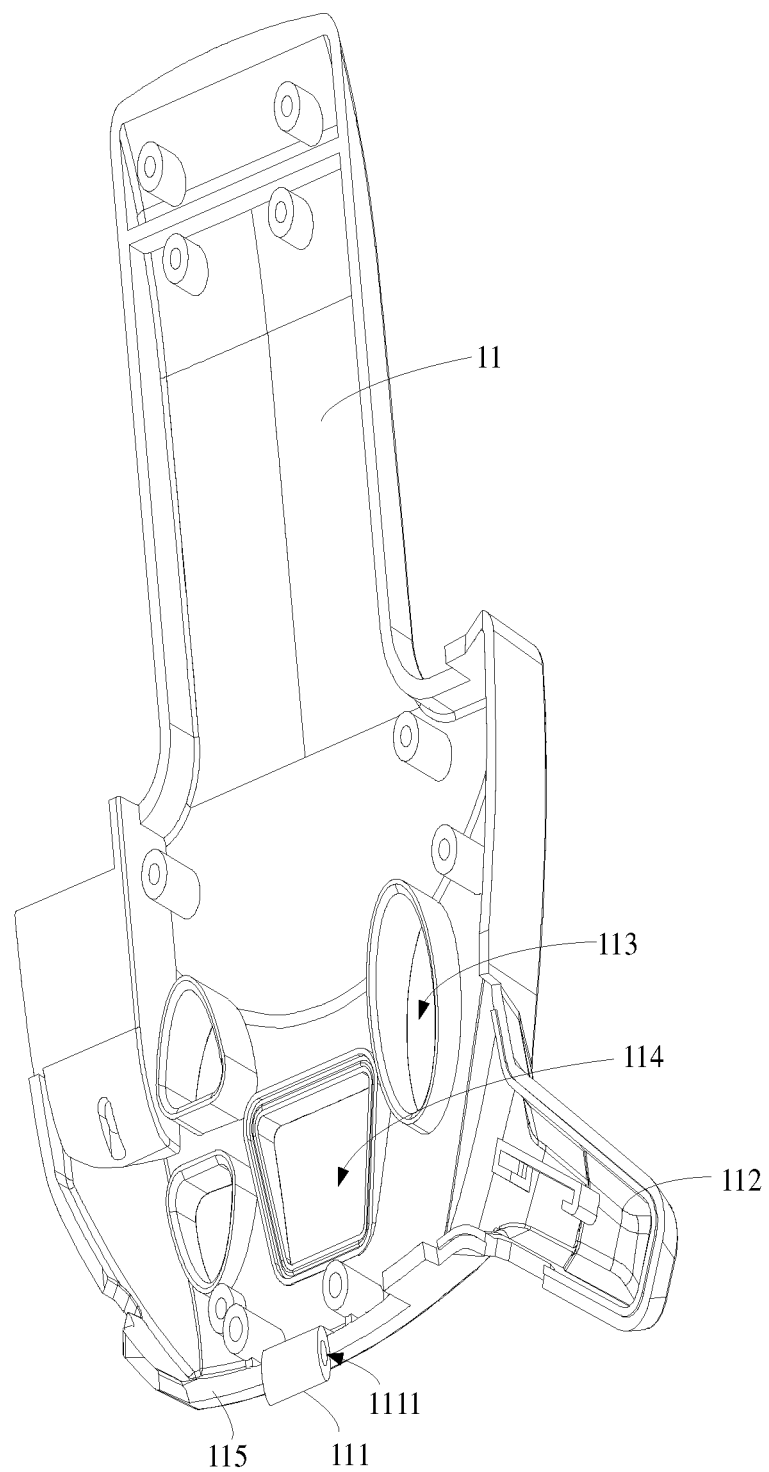
FIG. 4 is a structural diagram of an upper housing of the communication device of FIG. 1.
Figure 5:
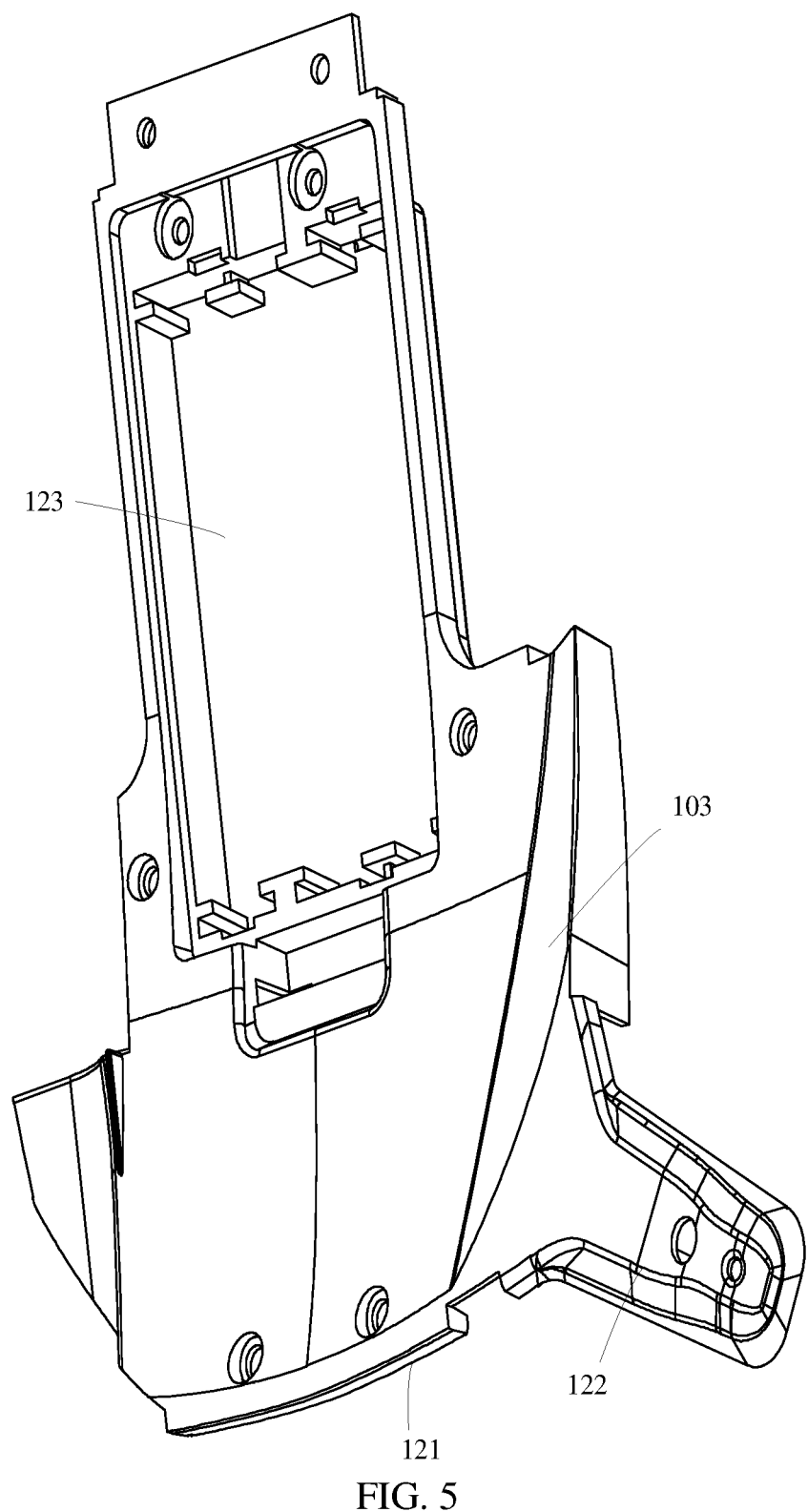
FIG. 5 is a structural diagram of a lower housing of the communication device of FIG. 1.
Figure 6:
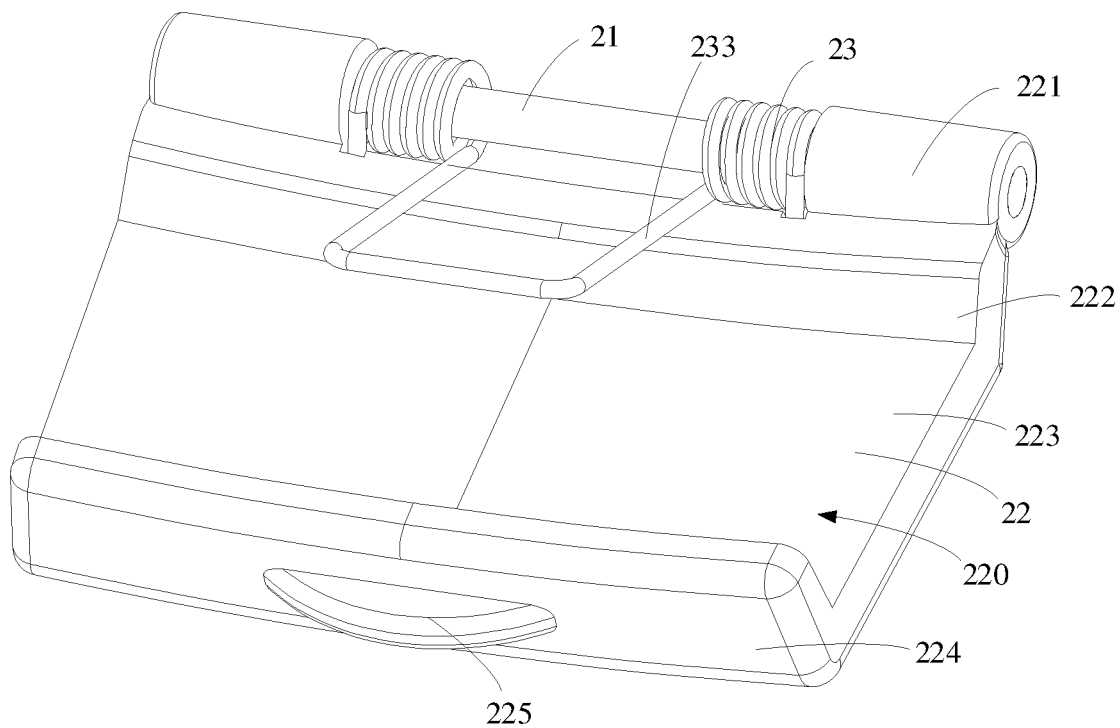
FIG. 6 is a structural diagram of a first mounting assembly of the communication device of FIG. 1.
Figure 7:
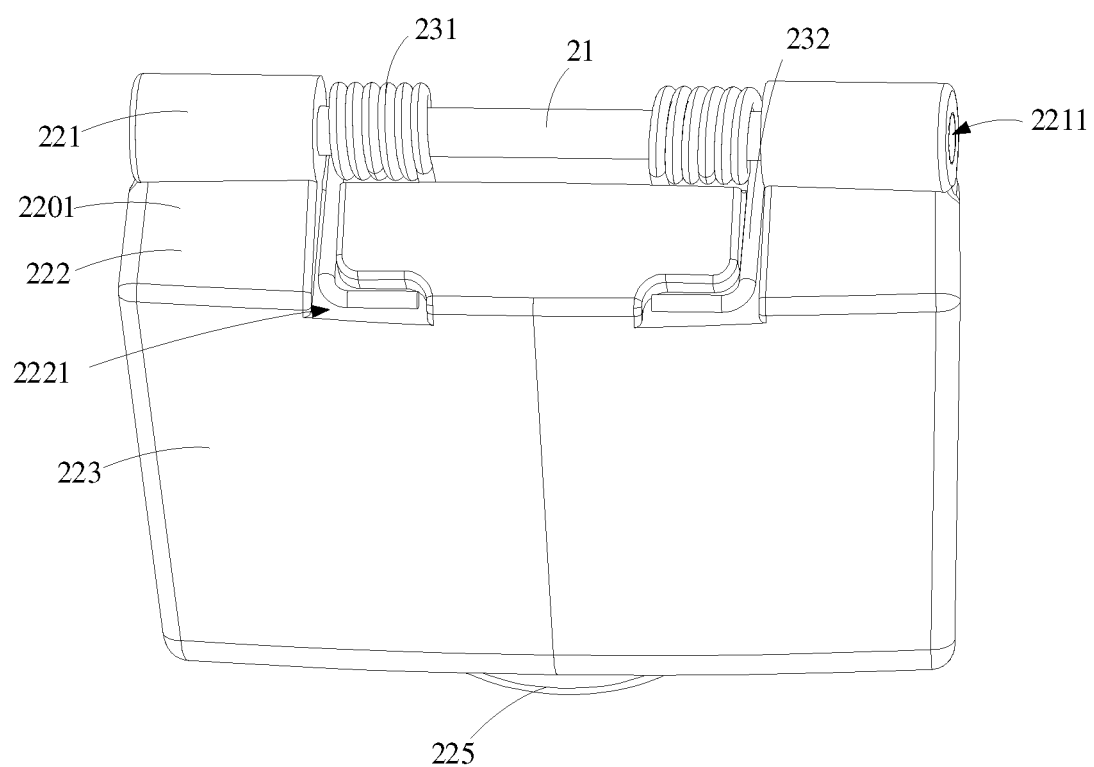
FIG. 7 is another structural diagram of the first mounting assembly of FIG. 6.
Figure 8:
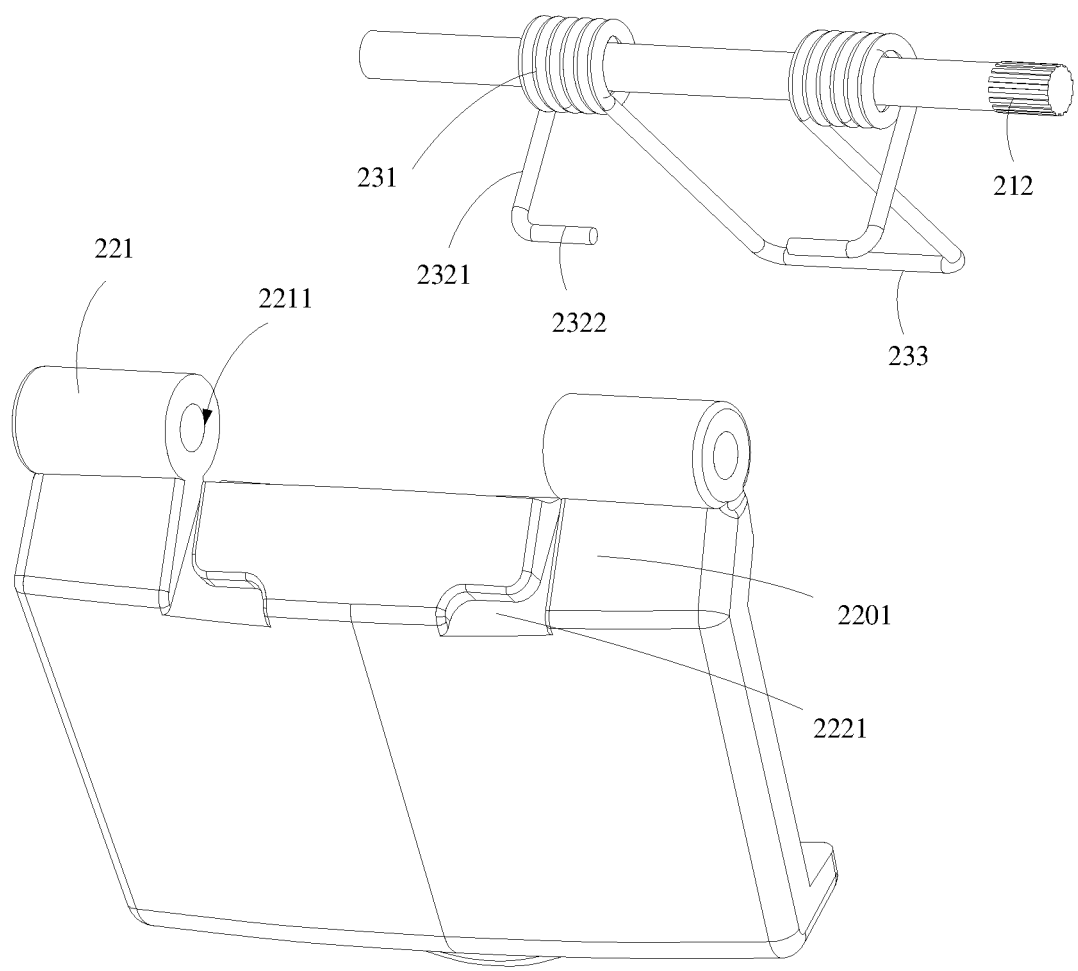
FIG. 8 is an exploded view of the first mounting assembly of FIG. 6.
Figure 9:
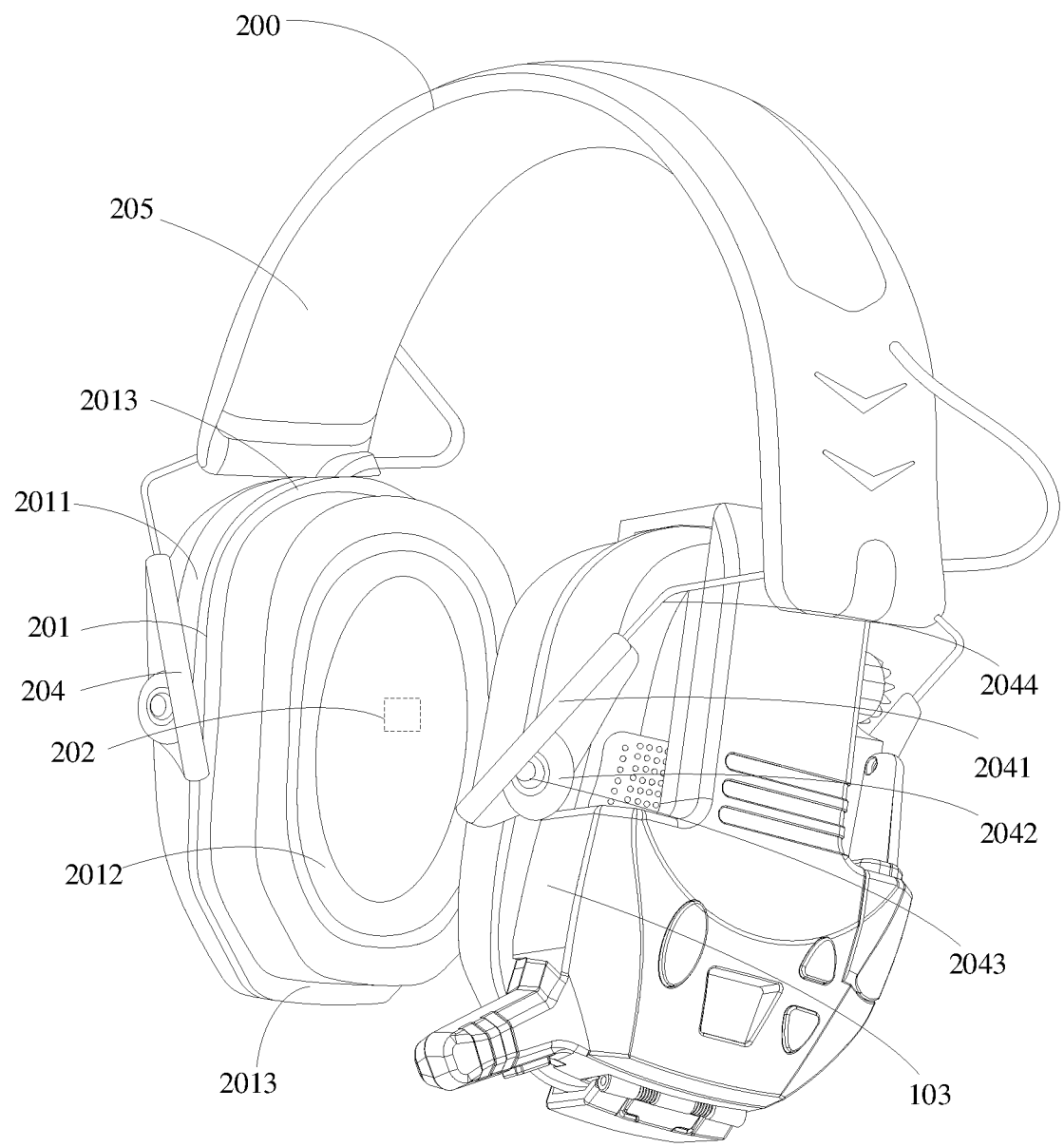
FIG. 9 is a structure diagram of a hearing protection equipment and the communication device according to an embodiment of the present disclosure, and the communication device is installed on the hearing protection equipment.
Figure 10:
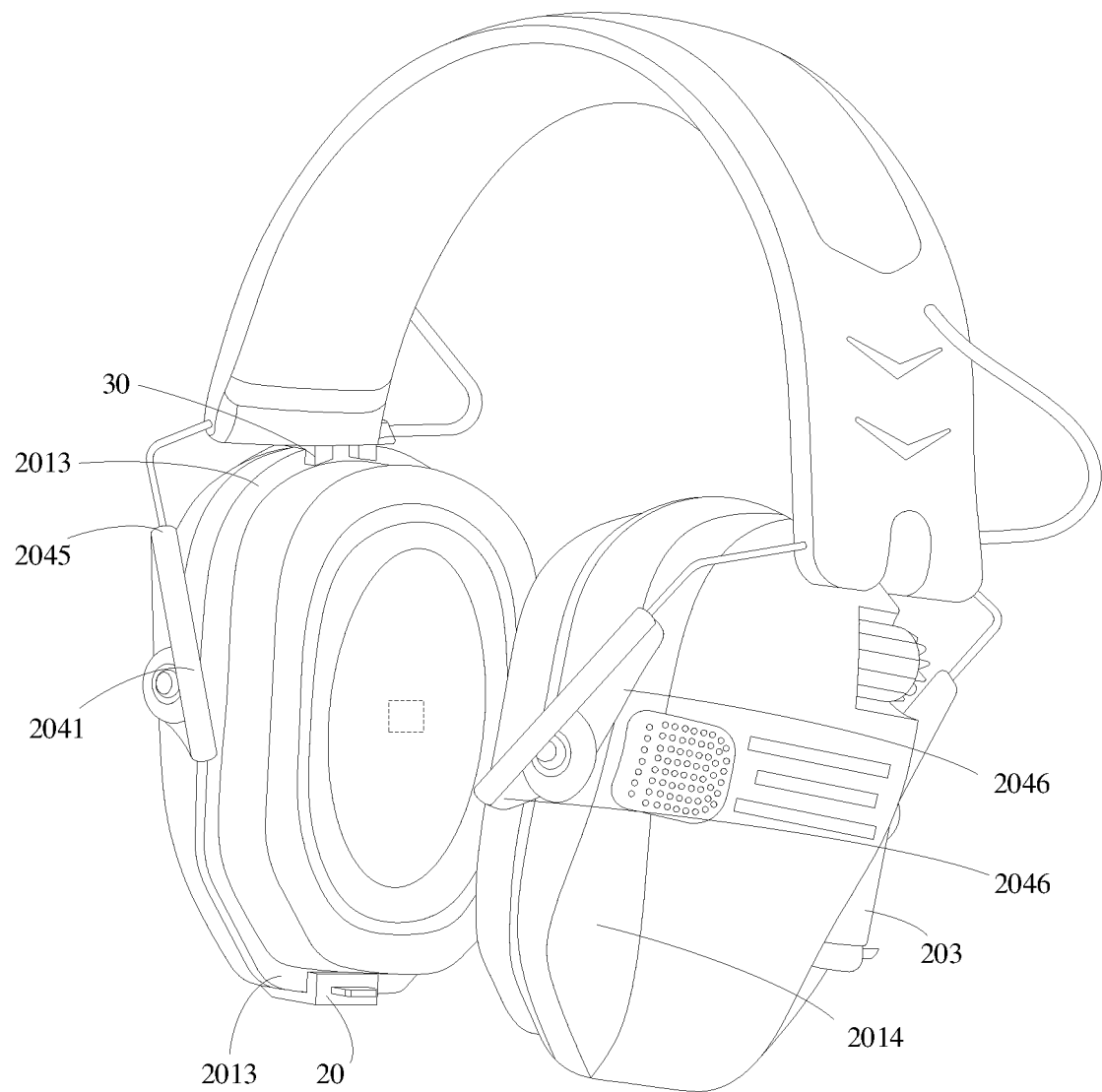
FIG. 10 is another structure diagram of the hearing protection equipment and the communication device of FIG. 9.

The realization of the aim, functional characteristics, advantages of the present disclosure are further described specifically with reference to the accompanying drawings and embodiments.

DETAILED DESCRIPTION

The technical solutions of the embodiments of the present disclosure will be clearly and completely described in the following with reference to the accompanying drawings. It is obvious that the embodiments to be described are only a part rather than all of the embodiments of the present disclosure. All other embodiments obtained by persons skilled in the art based on the embodiments of the present disclosure without creative efforts shall fall within the protection scope of the present disclosure.

Referring to FIGS. 1-10, the present disclosure provides a communication device 100 according to an embodiment, which may be installed on a hearing protection equipment 200. The hearing protection equipment 200 includes earmuffs 201, loudspeakers 202 arranged in the earmuffs 201, and an audio input member 203 arranged on a side of the earmuff 201 (referring to FIGS. 9 and 10).

The communication device 100 includes a housing 10, a first mounting assembly 20 rotatably arranged on a first end of the housing 10, a second mounting assembly 30 arranged on a second end of the housing 10, a microphone 40 for capturing an audio, a radio transceiver 50 configured to wirelessly transmit the audio captured by the microphone 40 to user and wirelessly receive one or more wireless signals carrying audio from the user, and an audio output member 60 connected to the audio input member 203 and configured to transmit the wireless signals carrying audio to the loudspeakers 202. The first mounting assembly 20 and the second mounting assembly 30 are releasably mounted on two ends of the earmuff 201 respectively to connect the communication device 100 with the hearing protection equipment 200.

The radio transceiver 50 can be set vertically. Specifically, the radio transceiver 50 is arranged in parallel with an axial direction of the housing 10 to make the communication device 100 compact.

The communication device 100 further includes at least one button 70, a display screen 80, and a power supply 90. The at least one button 70 may include an on-off button, a volume up button, a volume down button, etc. The power supply 90 may be a rechargeable battery, a lithium battery, a solar cell, or the like.

The housing 10 is substantially arc-shaped, and the housing 10 is matched with the earmuff 201 in structure. The housing 10 includes an upper housing 11, a lower housing 12 and a cover 13. The upper housing 11 includes a first receiving portion 112, the lower housing 12 includes a second receiving portion 122, and the microphone 40 is received in a space enclosed by the first receiving portion 112 and the second receiving portion 122. The first receiving portion 112 and the second receiving portion 122 can extend obliquely to a position adjacent to user's mouth, so that the microphone 40 can easily receive the wireless signal containing audio from the user. The upper housing 11 defines at least one first opening 113 and a second opening 114, the at least one button 70 is exposed through the at least one first opening 113, and the display screen 80 is exposed through the second opening 114.

After the power supply 90 is received in a receiving groove 123 defined in the lower housing 12, the cover 13 covers the power supply 90 to protect the power supply 90.

The earmuff 201 of the hearing protection equipment 200 includes a rigid housing 2011 and a flexible part 2012 detachably arranged on an inner side of the housing 2011. The flexible part 2012 is used to protect user's ear. Each of two ends of the housing 2011 is provided with a fixing part 2013. The first mounting assembly 20 and the second mounting assembly 30 are installed on the fixing parts 2013, respectively, so that the communication device 100 is installed on the hearing protection equipment 200.

The hearing protection equipment 200 further includes a bracket 205 connected between the two earmuffs 201 by at least one connecting assembly 204. A quantity of the at least one connecting assembly 204 may be four, the four connecting assemblies 204 201 are connected with two sides of the earmuffs 201, respectively. The connecting assembly 204 includes a first connecting portion 2041 connected with the earmuff 201, a second connecting portion 2042 connected with the first connecting portion 2041, a rotating portion 2043, and a third connecting portion 2044 configured to connect the first connecting portion 2041 with the bracket 205. A connecting end 2045 of the first connecting portion 2041 is connected with the third connecting portion 2044. The first connecting portion 2041 is protruded with at least one protrusion 2046 connected with the second connecting portion 2042. In detail, the first connecting portion 2041 is protruded with two protrusions 2046, and the second connecting portion 2042 is connected between the two protrusions 2046. The rotating portion 2043 is arranged on the housing 2011, and the second connecting portion 2042 is rotatably connected with the rotating portion 2043, so that the first connecting portion 2041 is rotatably connected with the housing 2011. The third connecting portion 2044 includes a straight section connected with the connecting end 2045 and a bending section connected with the bracket 205. The third connecting portion 2044 may be made of a bendable material, so that the first connecting portion 2041 can rotate easily.

The housing 10 further includes an engaging portion 103 protruded from a side of the housing 10. When the communication device 100 is mounted on the hearing protection equipment 200, the engaging portion 103 is clamped with an inclined surface 2014 of the housing 2011.

In the technical solution of the present disclosure, the communication device 100 includes the first mounting assembly 20 and the second mounting assembly 30, and the first mounting assembly 20 is rotatably arranged at the first end of the housing 10. When it needs to install the communication device 100 on the hearing protection equipment 200, the second mounting assembly 30 is installed on one fixing part 2013 of the hearing protection equipment 200; and the first mounting assembly 20 is rotated in a direction away from the housing 10, so that the hearing protection equipment 200 can be placed in the housing 10 easily, then the first mounting assembly 20 is rotated in a direction close to the housing 10 to install on the other fixing part 2013 of the hearing protection equipment 200 conveniently. Therefore, the installation process is simple and convenient. Further, as the first mounting assembly 20 is rotatably connected with the housing 10, when the first mounting assembly 20 is rotated in the direction away from the housing 10, the accommodating space 102 for accommodating the equipment 200 is expanded, so that the hearing protection equipment 200 of different sizes can be placed into the accommodating space 102, thus the communication device 100 has a better adaptability.

The first mounting assembly 20 includes a first connecting member 21 connected with the housing 10, a first mounting member 22, and an elastic member 23. The first mounting member 22 is rotatably connected with the first connecting member 21 by the elastic member 23. The first mounting member 22 is clamped with the earmuff 201 under the elastic force of the elastic member 23; the first mounting member 22 can be separated from the earmuff 201 after overcoming the elastic force of the elastic member 23.

The elastic member 23 includes at least one elastic body 231 arranged on the first connecting member 21, and at least one butting part 232 connected with the elastic body 231 and butted against the first mounting member 22. The first mounting member 22 rotates in a direction away from the housing 10 under a pressure, the first mounting member 22 rotates the butting part 232 to compress the elastic body 231; when the pressure applied to the first mounting member 22 is released, the elastic body 231 in a compressed state rotates the first mounting member 22 to an initial state.

The elastic body 231 can sleeve on the first connecting member 21.

The elastic member 23 further includes at least one fixing part 233 connected with the elastic body 231 and fixed on the housing 10. The elastic member 23 may include two opposite elastic bodies 231, two opposite butting parts 232, and two opposite fixing parts 233. The two opposite fixing parts 233 are connected to form a U-shaped structure.

The first mounting member 22 includes a receiving portion 2221, and the butting part 232 can be received in the receiving portion 2221. The butting part 232 includes a straight section 2321 connected with the elastic body 231 and a bending section 2322 connected with the straight section 2321. The two bending sections 2322 extend towards each other or extend in opposite directions. The receiving portion 2221 is matched with the butting part 232 in shape, that is, the receiving portion 2221 also has a straight section and a bending section.

One end of the upper housing 11 defines a notch 115. The upper housing 11 further includes a connecting element 111 connected with the first connecting member 21. The connecting element 111 extends out of the notch 115 to connect the first mounting member 22 with the housing 10. The connecting element 111 defines a through hole 1111, the first connecting member 21 is accommodated in the through hole 111, and the connecting element 111 is located between two elastic bodies 231. One end of the lower housing 12 is provided with a convex strip 121. When the upper housing 11 is connected with the lower housing 12, the convex strip 121 extends into the notch 115 to seal a part of the notch 115.

The first mounting member 22 includes a mounting portion 220 which may be a space, a groove, or a through hole, and the earmuff 201 is installed in the mounting portion 220. The at least one butting part 232 is butted against an outer surface 2201 of the mounting area 220. The first mounting member 22 is substantially U-shaped, and includes a first side wall 222, a bottom wall 223, and a second side wall 224. The first side wall 222, the bottom wall 223, and the second side wall 224 enclose the mounting portion 220. The fixing part 233 can extend above the mounting portion 220 from the gap between the first connecting member 21 and the first side wall 222. The outer surface of the second side wall 224 is provided with an operating portion 225 which can be a protrusion, a groove, or a through hole. The first side wall 222 may define the receiving portion 2221. The first side wall 222 is provided with at least one connecting part 221, the connecting part 221 defines an opening 2211, the first connecting member 21 is accommodated in the opening 2211. A quantity of the connecting part 221 may be two, and the elastic body 231 and the connecting element 111 can be located between the two connecting parts 221. At least one end of the first connecting member 21 is formed with a thread 212 to increase a friction between the first connecting member 21 and an inner wall of the opening 2211. The connecting portion 221 may be located on one side of the first side wall 222 away from the second side wall 224.

In the technical solution of the present disclosure, the first mounting assembly 20 includes the first connecting member 21 connected with the housing 10, the first mounting member 22, and the elastic member 23. The first mounting member 22 is rotatably connected with the first connecting member 21 by the elastic member 23. The first mounting member 22 is clamped with the earmuff 201 under the elastic force of the elastic member 23, the clamping strength between the first mounting member 22 and the earmuff 201 is increased. The first mounting member 22 can be separated from the earmuff 201 after overcoming the elastic force of the elastic member 23.

The second mounting assembly 30 includes a second connecting member 31 and a second mounting member 32. The second connecting member 31 is fixedly, detachably or rotatably connected with the housing 10. The second mounting member 32 is arranged on the second connecting member 31, and the second connecting member 31 is detachably installed on the second end of the earmuff 201.

The second mounting member 32 extends obliquely from one end of the second connecting member 31 to form another mounting portion (not marked) for mounting the earmuff 201.

It should be understood that the second mounting assembly 30 and the first mounting assembly 20 may have the same structure or different structures.

In the technical solution of the present disclosure, the second mounting assembly 30 includes the second connecting member 31 connected with the housing 10 and the second mounting member 32. The second mounting member 32 is detachably mounted on the second end of the earmuff 201, so that the first mounting member 22 and the second mounting member 32 can be respectively mounted on two ends of the earmuff 201.

The audio output member 60 includes a connecting head 61 and a connecting line 62. The connecting head 61 is communicated with the audio input member 203 for transmitting the wireless signal containing audio to the loudspeakers 202. The connecting line 62 is flexible, and the connecting head 61 is connected with an end of the connecting line 62 extending out of the housing 10. The connecting head 61 may be a connector.

In the technical solution of the present disclosure, the audio output member 60 includes the connecting head 61 and the connecting line 62, the connecting line 62 is flexible, so that user can easily connect the connecting head 61 with the audio input member 203.

Figure 11:
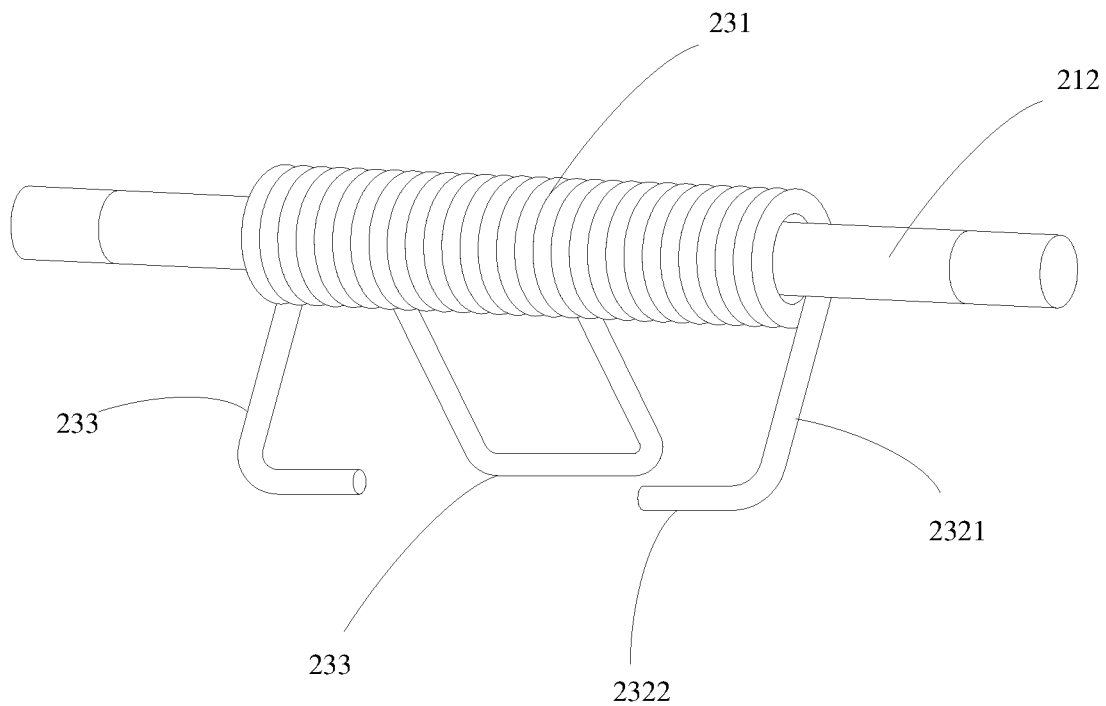
FIG. 11 is a structural diagram of an elastic member of the communication device according to another embodiment.

Referring to FIG. 11, the elastic member 23 of the first mounting assembly 20 may include an elastic body 231, two butting parts 232 spaced apart from each other, and a fixing part 233. The elastic body 231 is arranged on the first connecting member 21. The two butting parts 232 are butted against the first mounting member 22, and are respectively connected with the two ends of the elastic body 231. The butting part 232 includes a straight section 2321 connected with the elastic body 231 and two bending sections 2322 connected with the straight section 2321, and the two bending sections 2322 extend towards each other or extend in opposite directions. The receiving portion 2221 is matched with the butting part 232 in shape. The fixing part 233 can be located between the two butting parts 232. The fixing part 233 is substantially U-shaped.

Figure 12:
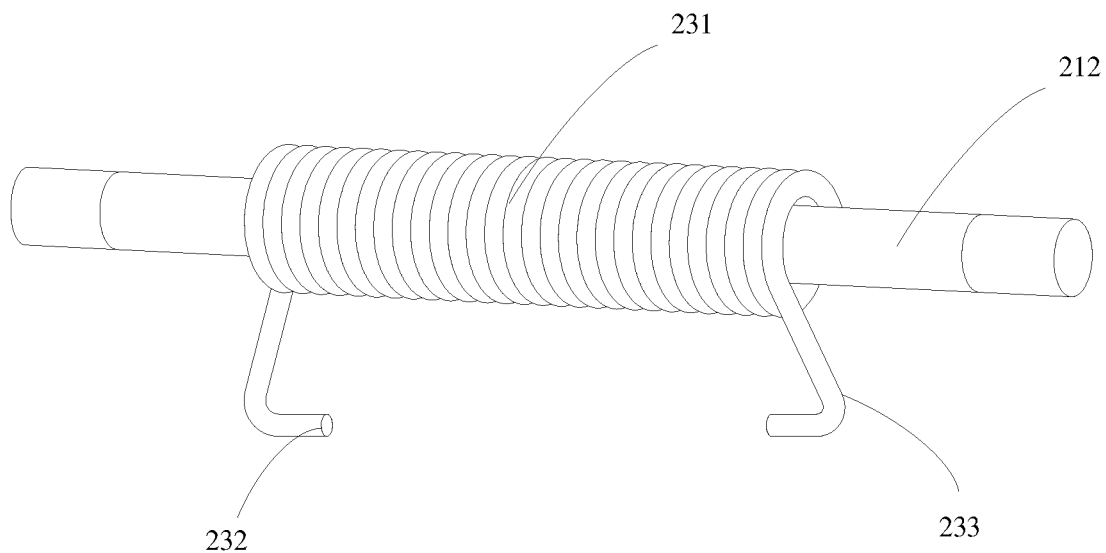
FIG. 12 is a structural diagram of an elastic member of the communication device according to a further embodiment.

Referring to FIG. 12, the elastic member 23 of the first mounting assembly 20 may include an elastic body 231, a butting part 232, and a fixing part 233. The elastic body 231 is arranged on the first connecting member 21. The butting part 232 is connected with one end of the elastic body 231, and the fixing part 233 is connected with the other end of the elastic body 231. The butting part 232 is butted against on the first mounting member 22. The fixing part 233 is fixed on the housing 10.

The present disclosure further provides a system for connecting the communication device 100 to the hearing protection equipment 200. In the system, the first mounting assembly 20 and the second mounting assembly 30 are releasably installed on the two fixing parts 2013 respectively, to connect the communication device 100 to the hearing protection equipment 200.

The above description is merely some embodiments. It should be noted that for one with ordinary skills in the art, improvements can be made without departing from the concept of the present disclosure, but these improvements shall fall into the protection scope of the present disclosure.

What is claimed is:

1. A communication device for a hearing protection equipment, the hearing protection equipment comprising at least one earmuff, at least one loudspeaker and an audio input member, wherein the communication device comprises:
- a housing;
- a first mounting assembly, rotatably arranged on a first end of the housing;
- a second mounting assembly, arranged on a second end of the housing, the first mounting assembly and the second mounting assembly are connected to two ends of the earmuff respectively to releasably connect the communication device with the hearing protection equipment;
- a microphone, configured for capturing an audio;
- a radio transceiver, configured for wirelessly transmitting the audio captured by the microphone to user and wirelessly receiving a wireless signal containing an audio from the user; and
- an audio output member, communicated with the audio input member and configured for transmitting the wireless signal containing the audio to the at least one loudspeaker, wherein the first mounting assembly comprises:
- a first connecting member, connected with the housing;
- an elastic member;
- a first mounting member, rotatably connected with the first connecting member by the elastic member, the first mounting member is coupled with the earmuff under an elastic force of the elastic member; and the first mounting member is separated from the earmuff after overcoming the elastic force of the elastic member.

2. The communication device according to claim 1, wherein the elastic member comprises:
- at least one elastic body, arranged on the first connecting member; and
- at least one butting part, connected with the elastic body and butted against the first mounting member, wherein when a pressure is applied on the first mounting member, the first mounting member rotates in a direction away from the housing, so that the butting part rotates to compress the elastic body; and
- the elastic body in a compressed state rotates the first mounting member to an initial state when the pressure applied on the first mounting member is released.

3. The communication device according to claim 1, wherein the at least one elastic body sleeves on the first connecting member.

4. The communication device according to claim 1, wherein the first mounting member comprises:
- a receiving portion, the at least one butting part is received in the receiving portion.

5. The communication device according to claim 1, wherein the butting part comprises:
- a straight section, connected with the elastic body; and
- a bending section, connected with the straight section.

6. The communication device according to claim 1, wherein the elastic member further comprises:
- at least one fixing part, connected with the elastic body and fixed on the housing.

7. The communication device according to claim 1, wherein the elastic member comprises:
- two elastic bodies, spaced apart from each other and arranged on the first connecting member; and
- two butting parts, spaced apart from each other and butted against the first mounting member, each butting part is connected with one corresponding elastic body.

8. The communication device according to claim 1, wherein the elastic member further comprises:
- a fixing part, fixed on the housing, two ends of the fixing part are connected with the two elastic bodies, respectively.

9. The communication device according to claim 1, wherein each butting part comprises:
- a bending section, the two bending sections extend towards each other or extend in opposite directions.

10. The communication device according to claim 1, wherein the elastic member comprises:
- an elastic body, arranged on the first connecting member; and
- two butting parts, spaced apart from each other and butted against the first mounting member, the two butting parts are both connected with the elastic body.

11. The communication device according to claim 1, wherein the elastic member comprises:
- an elastic body, arranged on the first connecting member;
- a butting part, connected with the elastic body and butted against the first mounting member; and
- a fixing part, connected with the elastic body and fixed on the housing.

12. The communication device according to claim 1, wherein the housing comprises:
- a connecting element, connected with the first connecting member to connect the first mounting member with the housing.

13. The communication device according to claim 1, wherein the second mounting assembly comprises:
- a second connecting member, connected with the housing; and
- a second mounting member, arranged on the second connecting member, and the second connecting member is detachably mounted on an end of the earmuff.

14. The communication device according to claim 1, wherein the audio output member comprises:
- a connecting head, communicated with the audio input member, and configured for transmitting the wireless signal containing the audio to the at least one loudspeaker; and
- a connecting line, connected with the connecting head, the connecting line is flexible.

15. The communication device according to claim 1, further comprising at least one of at least one button, a display screen and a power supply.

16. The communication device according to claim 1, wherein the housing is substantially arc-shaped, and the housing is adapted to the earmuff in shape.

17. A system for connecting a communication device to a hearing protection equipment, the system comprising:
- a communication device, comprising:
  - a housing;
  - a first mounting assembly, rotatably arranged on a first end of the housing; and
  - a second mounting assembly, arranged on a second end of the housing;
- and a hearing protection equipment, comprising:
  - at least one earmuff, comprising two fixing parts, the first mounting assembly and the second mounting assembly are installed on the two fixing parts respectively, to connect the communication device to the hearing protection equipment, wherein the first mounting assembly comprises:
- a first connecting member, connected with the housing;
- an elastic member;

a first mounting member, rotatably connected with the first connecting member by the elastic member, the first mounting member is coupled with the earmuff under an elastic force of the elastic member; and the first mounting member is separated from the earmuff after overcoming the elastic force of the elastic member.

18. The system according to claim 17, wherein the earmuff further comprises:

a rigid housing, comprising the two fixing parts; and a flexible part, arranged on the housing.

19. The system according to claim 17, wherein the communication device further comprises an audio output member; and the hearing protection equipment further comprises an audio input member, connected with the audio output member.

\* \* \* \* \*

(12) POST-GRANT REVIEW CERTIFICATE (303rd)

United States Patent
Xu

(10) Number: US 11,736,855 J1
(45) Certificate Issued: Feb. 5, 2026

(54) COMMUNICATION DEVICE AND SYSTEM FOR CONNECTING COMMUNICATION DEVICE TO HEARING PROTECTION EQUIPMENT

(71) Applicant: Hanwen Xu

(72) Inventor: Hanwen Xu

(73) Assignee: HANGZHOU ZH TECH CO., LTD.

Trial Number:

PGR2024-00034 filed May 21, 2024

Post-Grant Review Certificate for:

Patent No.: 11,736,855
Issued: Aug. 22, 2023
Appl. No.: 18/109,259
Filed: Feb. 13, 2023

The results of PGR2024-00034 are reflected in this post-grant review certificate under 35 U.S.C. 328(b).

POST-GRANT REVIEW CERTIFICATE
U.S. Patent 11,736,855 J1
Trial No. PGR2024-00034
Certificate Issued Feb. 5, 2026

AS A RESULT OF THE POST-GRANT REVIEW PROCEEDING, IT HAS BEEN DETERMINED THAT:

Claims 1-19 are cancelled.

\* \* \* \* \*